United States Patent [19]

Mensink et al.

[11] Patent Number: 4,665,919

[45] Date of Patent: May 19, 1987

[54] PACEMAKER WITH SWITCHABLE CIRCUITS AND METHOD OF OPERATION OF SAME

[75] Inventors: Kornelis A. Mensink, Brummen; Hendrik L. Brouwer, Dieren, both of Netherlands

[73] Assignee: Vitafin N.V., Curacao, Netherlands Antilles

[21] Appl. No.: 778,284

[22] Filed: Sep. 19, 1985

Related U.S. Application Data

[63] Continuation of Ser. No. 475,024, Mar. 14, 1983, abandoned.

[51] Int. Cl.$^4$ .............................................. A61N 1/36
[52] U.S. Cl. .............................................. 128/419 PG
[58] Field of Search ................................ 128/419 PG

[56] References Cited

U.S. PATENT DOCUMENTS

| | | | |
|---|---|---|---|
| 3,569,852 | 3/1971 | Berkovits | 128/696 |
| 3,949,758 | 4/1976 | Jirak | 128/419 PG |
| 4,114,627 | 9/1978 | Lewyn et al. | 128/419 PG |
| 4,121,055 | 10/1978 | Doherty | 179/15 A |
| 4,228,803 | 10/1980 | Rickards | 128/419 PG |
| 4,266,551 | 5/1981 | Stein | 128/419 PG |
| 4,305,396 | 12/1981 | Wittkampf et al. | 128/419 PG |
| 4,325,384 | 4/1982 | Blaser et al. | 128/708 |
| 4,381,786 | 5/1983 | Duggan | 128/419 PG |
| 4,390,022 | 6/1983 | Calfee et al. | 128/419 PG |
| 4,436,093 | 3/1984 | Belt | 128/419 PG |

FOREIGN PATENT DOCUMENTS 2026870 2/1980 United Kingdom .

Primary Examiner—William E. Kamm
Attorney, Agent, or Firm—Woodcock Washburn Kurtz Mackiewicz & Norris

[57] ABSTRACT

A device such as a cardiac pacemaker or other implantable biomedical device, and method of operation thereof, containing one or more switchable circuits. A control system, preferably incorporating a microprocessor, controls predetermined changes of the operating characteristics of the switchable circuits. In a cardiac pacer embodiment, a circuit such as the input amplifier can be switched to have different characteristics, e.g. filter setting and sensitivity, during predetermined portions of the pacer cycle. Further, the operation of a circuit can be monitored over a plurality of operating cycles, with controlled switching of the circuit characteristics as a function of cumulative monitored circuit performance. A specific example of the invention is shown for changing characteristics of a filter circuit used in a pacer which adjusts the pacer rate as a function of determined stimulus-T wave time interval.

5 Claims, 4 Drawing Figures

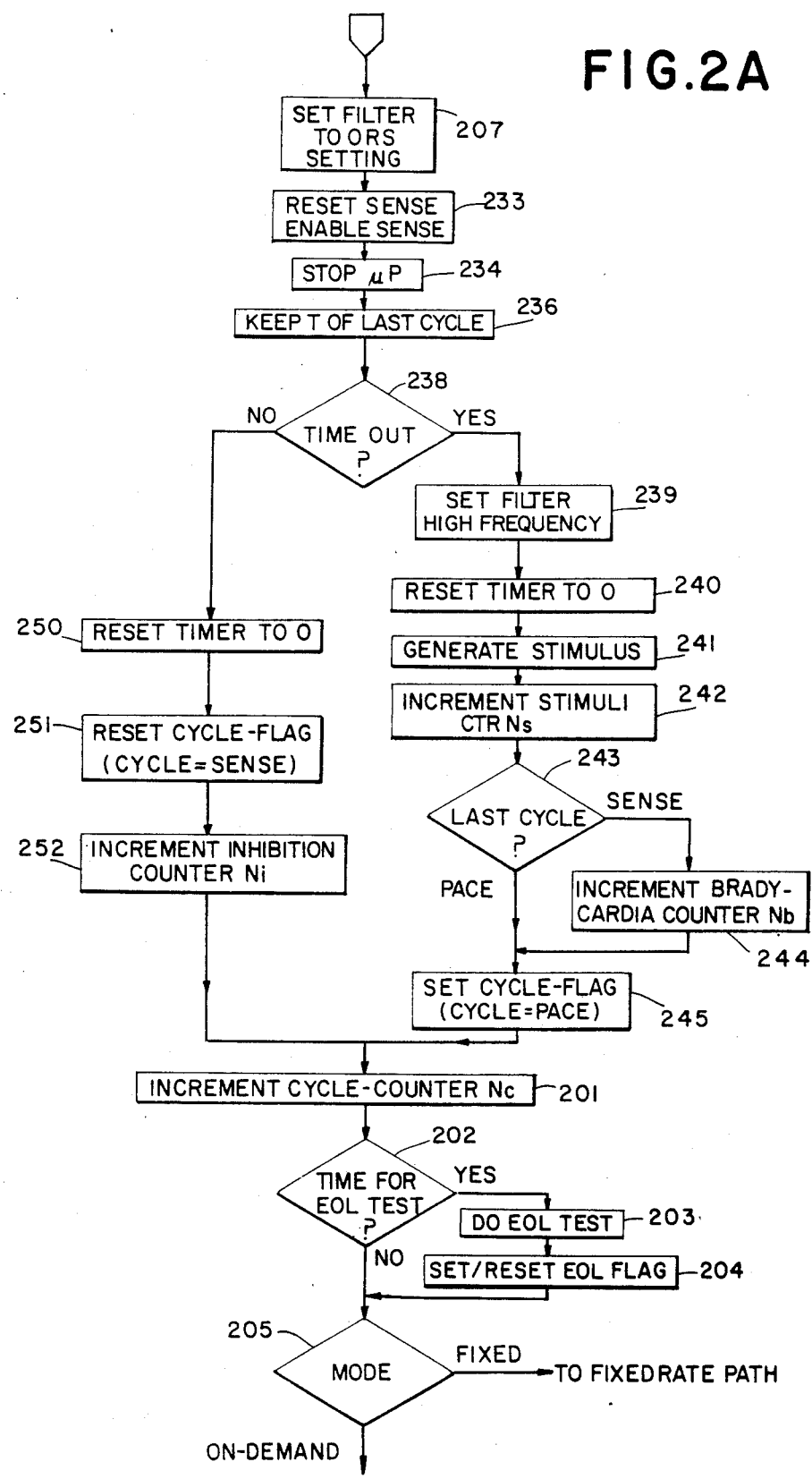

PACEMAKER WITH SWITCHABLE CIRCUITS AND METHOD OF OPERATION OF SAME

This is a continuation of application Ser. No. 475,024, filed Mar. 14, 1983 now abandoned.

BACKGROUND OF THE INVENTION

This invention lies in the area of cardiac pacers and method of operation of same, with means for varying operating characteristics of one or more circuits and, in particular, pacers and other implantable devices with microprocessor control for switching the characteristics of one or more circuits on a predetermined basis.

It is known that pacemakers, and other implanted devices generally, have a need to respond to different types of sensed signal information. Thus, for example, in the pacemaker embodiment, where the implanted device operates on a cyclical basis, it may be desirable to change the operating characteristics of the circuit or circuits which sense the patient-generated signals, either within each cycle of operation, or over a period of time. In the prior art it is well known that parameters can be programmed externally, but such programming does not meet the objective of this invention for changing one or more circuit characteristics during each cycle, nor does programming provide for automatic response to sensed patient conditions.

While it is known that programmable circuits are available in other art areas, there has been no use or incorporation of controllable or switchable circuits into implantable devices for more efficient use thereof. For devices such as cardiac pacemakers, muscle stimulators, automatic drug dispensers, etc., there is a substantial need for the advantages to be gained by proper use of automatic switching, or by controlling the characteristics of circuits, e.g. changing filter characteristics. By use of a microprocessor incorporated with the implanted device, it is possible to optimize circuit operation in a manner which has heretofore been unavailable to the art.

SUMMARY OF THE INVENTION

It is an object to provides one or more controllable circuits which can be switched on a periodic or non-periodic basis to provide better response characteristics, particularly in an implanted device.

It is another object of this invention to provide microprocessor control for changing the circuit characteristics of one or more circuits within a cycle of a device such as a cardiac pacemaker which operates on a cyclic basis.

It is another object of this invention to provide microprocessor control of a sense amplifier used for detection of evoked responses and T waves in a cardiac pacer, as part of a pacer system for optimizing pacer rate control.

It is another object of this invention to provide microprocessor control of circuit characteristics, such as the frequency setting of an amplifier filter for amplifying sensed cardic signals, or for controlling sensitivity of an input amplifier, over a plurality of cardiac cycles.

In accordance with the above objects, the invention provides one or more switchable circuits, and control means for switching same. In one embodiment an improved programmable filter and QRS sense amplifier circuit is provided with means for switching the filter from its normal response to a fast recover characteristic during a given time period following delivery of a stimulus. The fast recovery of the amplifier filter combination is achieved by switching the circuit to achieve a shorter time constant response. Microprocessor control, and a method thereof, is provided for switching one or more circuits in a cardiac pacer to change the characteristics of such one or more circuits within a pacer cycle, thereby providing optimized performance. Microprocessor control, and a method thereof, is also provided for changing the characteristics of one or more circuits over a period of time, i.e. over a plurality of pacer cycles, to optimize the circuit characteristics as a function of sensed or measured circuit performance. In another embodiment, a cardiac pacer is provided, having microprocessor control of a sense amplifier, for detecting evoked responses following evoked stimuli, as well as sensing of T waves, and means for control of the rate of delivery of stimulus pulses as a function of measured stimulus-T wave time.

BRIEF DESCRIPTION OF THE DRAWINGS

FIG. 2A is a portion of a flow diagram showing microprocessor control of a pacer system which incorporates a change of one or more circuits during each cycle of operation.

DESCRIPTION OF THE PREFERRED EMBODIMENTS

Figure 1:
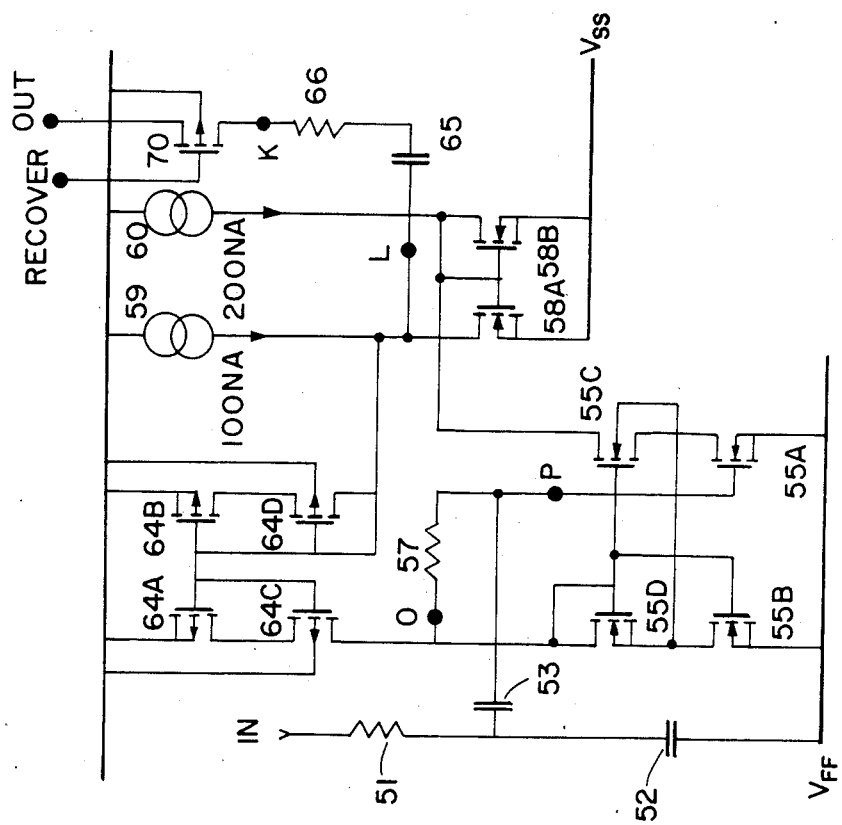
FIG. 1 is a circuit diagram of a programmable filter and sense amplifier for use in a cardiac pacemaker.

Referring now to FIG. 1, there is shown a circuit diagram of a QRS detection amplifier adapted for use in a cardiac pacemaker, having a programmable filter. In general, such a programmable filter may use one or more time constant-determining networks, e.g. resistor and capacitor, transconductance and capacitor, frequency-controlled charge switch and capacitor, etc. A switching means, preferably controlled by a logic sequencer such as provided by a microprocessor, turns on and off one or more of the time constant networks, or changes the switching frequency of the frequency-controlled time constant. In this manner, the filter characteristic, or frequency response of the circuit can be changed as desired.

In the circuit of FIG. 1, the circuit is designed to sense QRS waves from a patient, and to insure that there are no artifacts due to stimulus pulses after the refractory period. By using a "restore" switch, the active filter bandpass characteristic is shifted to a higher frequency, and lower gain, during a predetermined time following the stimulus, e.g. 60 msec. The resulting effect of this switching is a fast recovery of the amplifier-filter combination, because of the shorter time constant during the recovery period. Depending upon the energy of the stimulus pulse delivered, an improvement of up to a factor of 2 can be achieved in the response time, which provides a substantial improvement in avoiding detection of artifacts due to the stimulus pulses.

Referring specifically to the circuitry, the input is provided at the terminal connected to resistor 51. The other side of 51 is coupled through capacitor 52 to the $V_{EE}$ line, and through capacitor 53 to point P, which is the input to an input amplifier comprised of FET transistors 55A, 55B, 55C and 55D. Transistors 55B and 55D provide a virtual 1 megohm resistence between node O and the $V_{EE}$ line. The output from the input amplifier is taken from transistor 55C and inputted to the common gates of transistors 58A, 58B, which together provide an inverting amplifier. The drain of transistor 58A is connected to current source 59, which provides 100 nA; the drain of 58B is connected to the output of current source 60, which provides 200 nA.

The output of the inverting amplifier, at node L, is connected in two paths. A feedback path goes through the circuit made up of 4 FETs 64A–D, to provide a feedback signal at node O, which is connected through resistor 57 to node P at the input to the input amplifier. The output circuit connected to node L comprises capacitor 65 in series with resistor 66, which in turn is connected through FET 70, the source of which is connected as the output terminal. The gate is connected to receive a "recover" signal, which gate switch 70 in or out of the circuit. When FET 70 is controlled to conduct, RC combination 65, 66 is in the circuit; when the switch is opened by the recover signal, there is no signal at the output and the circuit recovers quickly from any transients introduced by the stimulus signal.

For the circuit of FIG. 1, the following typical values are used for the resistors and capacitors:

| | |
|---|---|
| Resistor 51 - 100K ohm | Capacitor 52 - 10 nano farads |
| Resistor 57 - 15 M ohm | Capacitor 53 - 2.7 nano farads |
| Resistor 66 - 270K ohm | Capacitor 65 - 22 nano farads |

The transconductance from node P to node L is about 15 nA/mV; from node L to node O about 1.0 nA.

Figure 2B:
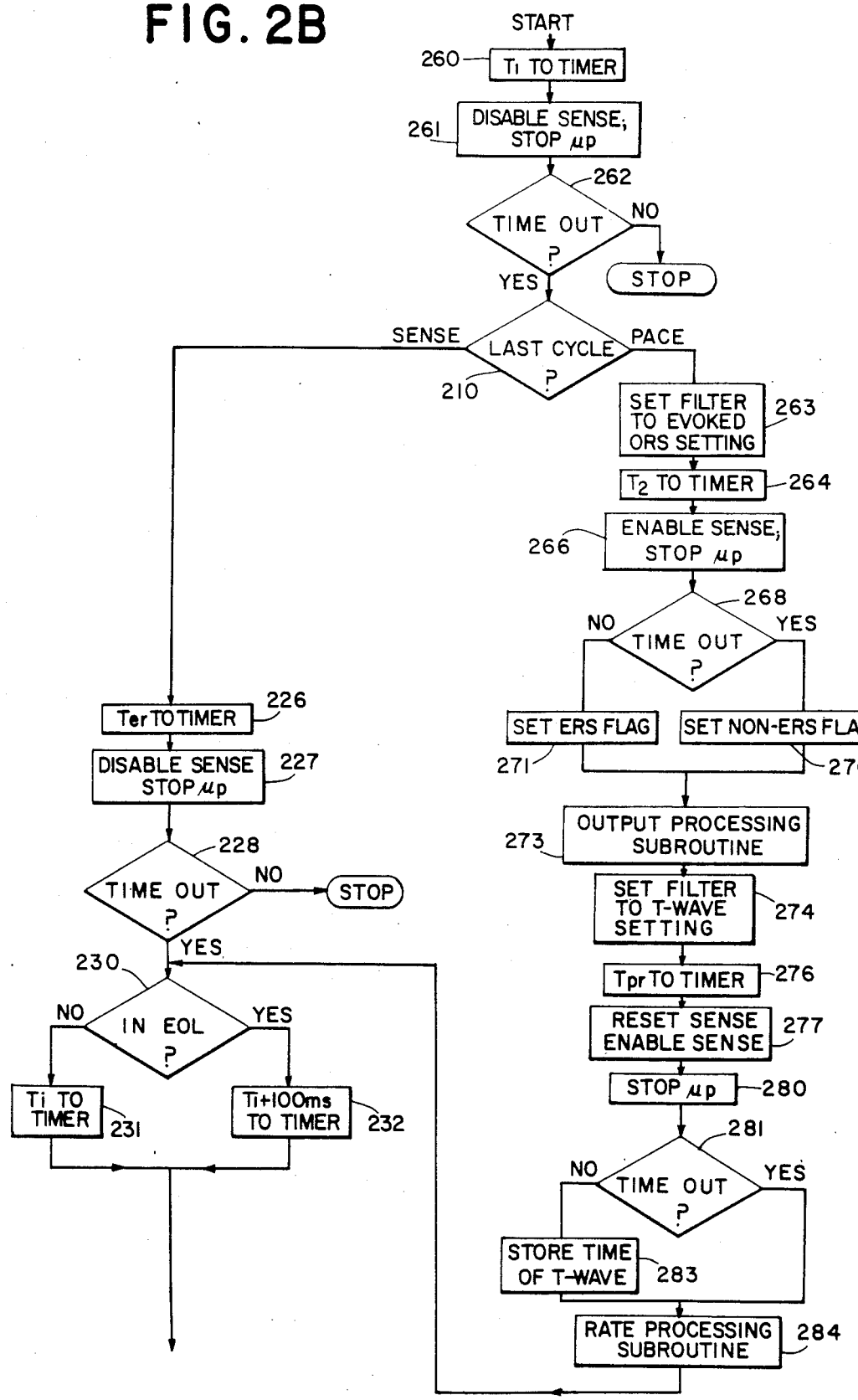
FIG. 2B is a portion of a flow diagram showing microprocessor control of a cardiac pacer which adjusts the pacing rate as a function of sensed stimulus-T wave times, incorporating control of one or more circuit characteristics.
Figure 2C:
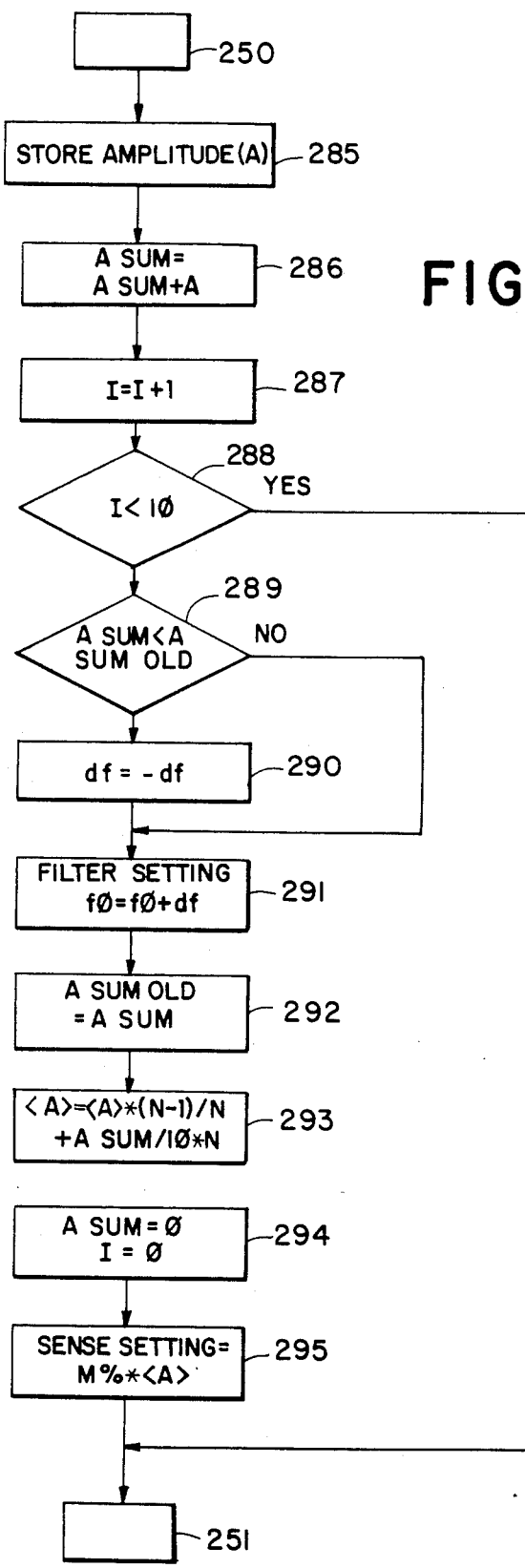
FIG. 2C is a flow diagram of microprocessor control of an implanted device, such as a cardiac pacemaker, which operates cyclically, incorporating control of circuit characteristics effected over a time period of more than one cycle.

The block diagrams of FIGS. 2A, 2B and 2C are modifications of the block diagram shown in FIGS. 2A and 2B of U.S. patent application Ser. No. 436,411, assigned to the same assignee, which application is incorporated herein by reference. The detailed description of the flow diagram of FIGS. 2A and 2B of that application describes a cycle of operation of the pacemaker. The block diagrams shown in FIGS. 2A–2C of this application embody modifications to or additions of that cycle flow diagram. FIGS. 2a and 2b may be read together as one flow diagram covering a cycle of pacer operation.

Referring to FIG. 2A, there is illustrated an example of a microprocessor controlled cardiac pacemaker which changes filter characteristics and/or sensitivity within the pacer cycle. The program, as illustrated, starts at a time just after the time out of the pacer refractory period. At block 207, the filter of the input amplifier, connected to receive a patient cardiac signal, is set to an appropriate QRS setting, i.e., set to an appropriate bandpass for detecting a patient QRS signal. At block 233, the microprocessor enables sensing through the input amplifier, and, for example, sets the sensitivity at 2 mV. At block 234, the microprocessor is stopped to await either timeout or a sensed QRS. When either of these events occurs, the microprocessor picks up at block 236 and records the time T of the last cycle, and then determines whether a timeout has occurred, at block 238.

If a timeout has occurred, meaning there has been no natural patient beat, the program block branches to the right. In preparation for generating the stimulus, the filter of the input amplifier is first set to a high frequency characteristic, at block 239, in order to quickly damp out any artifacts produced by the generated stimulus. Thereafter the pacer timer is set to zero at block 240, and the stimulus is generated at block 241. The pacer cycles through the remainder of the program, and the filter is reset to the normal QRS setting at block 207 during the next cycle.

Referring to FIG. 2B, there is shown a block diagram of a further portion of a pacer control program providing for controlling the rate of delivered stimulus pulses as a function of sensed stimulus-T wave time intervals. Reference is made to U.S. Pat. Nos. 4,228,803 and 4,305,396, which are incorporated herein by reference. At the top of FIG. 2B, the routine starts after stimulus delivery provided in FIG. 2a. A time delay is introduced at block 260, corresponding to the delay between the stimulus and the start of evoked response sensing. The sense amplifier is disabled at block 261, and the microprocessor is stopped to wait for the evoked response. At block 262, the microprocessor determines whether the timer has timed out. If yes, and the last cycle was a pace cycle, as determined at 210, the pacer control branches to the right. At block 263, a switchable filter such as that of FIG. 1 with a multiple of parallel output circuits is set to the evoked QRS setting, i.e., to a filter characteristic optimally designed to detect an evoked QRS. A period $T_2$ is put into the timer at 264, during which the pacer looks for the evoked response. The sense amplifier is enabled at block 266, for example with a sensitivity of 8 mV. At block 268, it is determined whether the timer has timed out. If no, meaning that an evoked response was detected, the ERS flag is set at block 271. If yes, meaning that there was no evoked response, the non-ERS flag is set at 270. Following this, at block 273, the microprocessor goes through the output processing subroutine, to change the stimulus magnitude if required to achieve heart capture. At block 274, the filter characteristic of the input amplifier is modified to a characteristic adapted for detecting the T wave portion of the heart signal. Following this, at block 276, a time interval $T_{PT}$ corresponding to the T wave time is set into the timer, and at block 277 the sense amplifier is enabled at a sensitivity of, for example, 1 mV. The microprocessor is stopped at 280, and is started again at 281 either by a sensed T wave or by timing out. If it is not timed out, meaning that a T wave was sensed, the time of this T wave in relation to the delivered pulse stimulus is stored at 283. At block 284, the microprocessor goes through a rate subprocessing routine to change the pacer rate, as set forth in U.S. Pat. No. 4,228,803.

Referring to FIG. 2C, there is illustrated a routine for shifting the filter characteristic of a pacer input filter, as a function of monitored operation of the filter over a plurality of pacer cycles. The portion of the routine shown in FIG. 2C falls between blocks 250 and 251 of FIG. 2B in Ser. No. 436,411. While, in this example, the center frequency only of the filter is shifted, it is to be understood that in a more complicated circuit modification can be utilized for shifting the lower and higher cut off points independently. The example of FIG. 2C is by way of illustration only, for showing switchable control of a circuit characteristic as a function of monitored circuit performance, i.e., a measured value of circuit operation, over a plurality of cycles.

Referring specifically to FIG. 2C, following block 250 the amplitude of the received input wave, QRS, P, etc., is stored at 285. At block 286, a new sum designated A SUM is accumulated by adding the just received amplitude A to the prior sum. At block 287, the number of iterations I is incremented by 1. In the illustration, the routine iterates 10 times in order to accumulate a sum, but it is to be understood that the number of iterations is a matter of choice. At block 288, it is determined whether I is less than 10. If yes, more cycles are to be measured, and the routine branches directly to block 251. If no, meaning that 10 measurements have now been accumulated, the program proceeds to block 289, where it is determined whether A SUM is less than the prior, or old A SUM. If no, meaning that A SUM has increased, the routine branches to block 291. If yes, the routine first performs the operation at block 290 of changing the incremental frequency deviation from +df to −df. Note that at block 289 the program is checking to see whether the new cumulative amplitude has improved or not relative to the previous cumulative amplitude. If yes, then at block 291 the filter setting is changed in the same direction by the small step df, by setting the new center frequency f0 to f0+df. If the cumulative amplitude is less, then it is presumed that the center frequency should be shifted in the other direction, which is accomplished by making df= −df. Then, at block 292, the microprocessor stores the cumulated A SUM as A SUM OLD. At block 293, the mean amplitude <A> is updated by a predetermined algorithm which is a matter of choice. Following this, at block 294, the present values of A SUM and I are set to 0. At block 295, the sensitivity setting is automatically re-programmed to a fixed safe percentage M of the measured mean amplitude. Following this, the routine proceeds to block 251, and continues.

There have thus been set forth examples of preferred embodiments of the invention, for microprocessor control of switchable characteristics of 1 or more circuits in a device such as a cardiac pacemaker. Reference is made to U.S. Pat. No. 4,305,396, incorporated by reference, for examples of other signal characteristics which may be measured by a cardiac pacemaker, and for which specific circuit characteristics are switched into and out of operation. Although a microprocessor embodiment has been shown by way of illustration, it is understood that other equivalent digital or analog means may be incorporated into a device in accordance with this invention, providing switchable circuits, characteristics and control therefor as used in the claims, the term /circuit characteristics/ means frequency response, sensitivity, gain, etc., and it does not include an operating parameter such as time set in a timing circuit.

We claim:

1. A cardiac pacemaker having sensing means for sensing patient cardiac signals from a predetermined cardiac source and pulse means for producing stimulus pulses, said signals having first and second periodic signal portions, said sensing means having at least one circuit switchable to at least two respective circuit characteristics corresponding to said first and second signal portions, and microprocessor control means connected to said sensing means and said pulse means for controlling the operation of said pacemaker on a cyclical basis, said microprocessor control means comprising means connected to said circuit for switching the circuit characteristics of said circuit to provide different characteristics during each of said signal portions of each pacemaker cycle.

2. The cardiac pacemaker as described in claim 1, having means for measuring stimulus-T wave time during each pacing cycle, and means for controlling pacing stimulus rate as a function of said measured time, wherein said switchable circuit is the input amplifier, and said microprocessor control means has means connected to said input amplifier for controlling the frequency characteristic of said input amplifier to have respective different characteristics during sensing of evoked QRS and T waves.

3. The cardiac pacemaker as described in claim 1, wherein said switchable circuit has a plurality of different frequency characteristics including a natural QRS response, fast response, T-wave response and evoked heartbeat response, and wherein said control means has means for selecting any combination of said responses and for controlling said switchable circuit in accordance with said selecting.

4. A cardiac pacemaker having sensing means for sensing a patient cardiac signal and pulse means for producing stimulus pulses, said sensing means having at least one circuit switchable to at least two respective circuit characteristics, monitoring means for monitoring the response of said circuit to said cardiac signal over a plurality of pacemaker cycles and determining a measure of said response over said cycles, and microprocessor control means connected to said sensing means, said pulse means and said monitoring means for controlling the operation of said pacemaker on a cyclical basis, said microprocessor control means comprising switching means connected to said switchable circuit for switching its circuit characteristics as a function of said measure.

5. The pacemaker of claim 4 characterized by said switchable circuit having an amplifier for amplifying a detected cardiac signal, said amplifier having a filter switchable to at least two different frequency responses, one of said switchable responses being a high frequency response for fast damping out of artifacts and another of said switchable responses being a signal response to a detected cardiac signal, said switching means comprising means for controllably switching said filter to said high frequency response during a first portion of the cycle and to said signal response during a second portion of the cycle.

* * * * *